US00PP18436P2

(12) United States Plant Patent
De Boer

(10) Patent No.: US PP18,436 P2
(45) Date of Patent: Jan. 15, 2008

(54) ***ERYNGIUM* PLANT NAMED 'LITTLE BLUE WONDER'**

(50) Latin Name: *Eryngium planum*
Varietal Denomination: Little Blue Wonder

(75) Inventor: Huibert Anne De Boer, Rijnsburg (NL)

(73) Assignee: Fa. H.A. de Boer & Molta B.V., Rijnsburg (NL)

( * ) Notice: Subject to any disclaimer, the term of this patent is extended or adjusted under 35 U.S.C. 154(b) by 0 days.

(21) Appl. No.: 11/351,850

(22) Filed: Feb. 10, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

UPOV PBR 20030996 filed May 26, 2003.*

* cited by examiner

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Eryngium* plant named 'Little Blue Wonder', characterized by its compact and upright plant habit; freely branching growth habit; and dark blue purple-colored flowers.

1 Drawing Sheet

Botanical designation: *Eryngium planum.*
Cultivar denomination: 'Little Blue Wonder'.

BACKGROUND OF THE INVENTION

The present invention relates to a new and distinct cultivar of *Eryngium* plant, botanically known as *Eryngium planum,* and hereinafter referred to by the name 'Little Blue Wonder'.

The new *Eryngium* is a naturally-occurring whole plant mutation of the *Eryngium planum* cultivar Fluela, disclosed in U.S. Plant Pat. No. 7,218. The new *Eryngium* was discovered and selected by the Inventor in August, 2001 in a controlled environment in Wassenaar, The Netherlands from within a population of plants of 'Fluela'.

Asexual reproduction of the new *Eryngium* by divisions at Rijnsburg, The Netherlands since January, 2003, has shown that the unique features of this new *Eryngium* are stable and reproduced true to type in successive generations.

BRIEF SUMMARY OF THE INVENTION

The following traits have been repeatedly observed and are determined to be the unique characteristics of 'Little Blue Wonder'. These characteristics in combination distinguish 'Little Blue Wonder' as a new and distinct cultivar:

1. Compact and upright plant habit.
2. Freely branching growth habit.
3. Dark blue purple-colored flowers.

Plants of the new *Eryngium* differ primarily from plants of the parent, the cultivar Fluela, in the following characteristics:

1. Plants of the new *Ergyngium* are more compact than plants of the cultivar Fluela.
2. Plants of the new *Eryngium* have narrower leaves than plants of the cultivar Fluela.

3. Plants of the new *Eryngium* have shorter flowering stems than plants of the cultuvar Fluela.

Plants of the new *Eryngium* can be compared to plants of the *Eryngium* cultivar Sapphire Blue, disclosed in U.S. Plant Pat. No. 11,088. Plants of the new *Eryngium* differ from plants of the cultivar Sapphire Blue in the following characteristics:

1. Plants of the new *Eryngium* are more compact than plants of the cultivar Sapphire Blue.
2. Plants of the new *Eryngium* have smaller leaves than plants of the cultivar Sapphire Blue.
3. Plants of the new *Eryngium* and the cultivar Sapphire Blue differ in leaf coloration.
4. Plants of the new *Eryngium* flower more freely and earlier than plants of the cultivar Sapphire Blue.

BRIEF DESCRIPTION OF THE PHOTOGRAPHS

The accompanying colored photographs illustrate the overall appearance of the new *Eryngium,* showing the colors as true as it is reasonably possible to obtain in colored reproductions of this type. Colors in the photographs may differ slightly from the color values cited in the detailed botanical description which accurately describe the colors of the new *Eryngium.*

The photograph at the top of the sheet comprises a side perspective view of a typical flowering plant of 'Little Blue Wonder'.

The photograph at the bottom of the sheet comprises close-up views of the lower (top left) and upper (top right) surfaces of typical leaves and a typical flowering stem (bottom) of 'Little Blue Wonder'.

DETAILED BOTANICAL DESCRIPTION

The cultivar 'Little Blue Wonder' has not been observed under all possible environmental conditions. The phenotype may vary somewhat with variations in environment such as temperature, daylength and light intensity, without, however, any variance in genotype.

In the following description, color references are made to The Royal Horticultural Society Colour Chart, 2001 Edition, except where general terms of ordinary dictionary significance are used. Plants used for the photographs and the following description were grown in Noordwijkerhout, The Netherlands, in an outdoor nursery under commercial practice during the summer and autumn for about six months with average day temperatures ranging from 18° C. to 27° C. and night temperatures ranging from 12° C. to 18° C.

Botanical classification: *Eryngium planum* cultivar 'Little Blue Wonder'.

Parentage: Naturally-occurring whole plant mutation of the *Eryngium planum* cultivar Fluela, disclosed in U.S. Plant Pat. No. 7,218.

Propagation:

*Type.*—By divisions.

*Time to produce a rooted young plant.*—About 80 days at 12° C.

*Root description.*—Thick, fibrous; brown in color.

*Rooting habit.*—Freely branching; dense.

Plant description:

*Form/growth habit.*—Compact and upright plant habit; freely branching and flowering habit. Vigorous growth habit.

*Branching habit.*—About five to ten lateral branches per plant.

*Plant height at flowering.*—About 35 cm.

*Plant diameter at flowering.*—About 20 cm.

*Vegetative leaf description.*—Arrangement: Alternate, simple. Length: About 6 cm. Width: About 4.5 cm. Shape: Oblong. Apex: Acuminate. Base: Cordate. Margin: Crenate. Texture, upper and lower surfaces: Smooth, glabrous; leathery. Color: Developing and fully expanded foliage, upper surface: 137A; venation, 147B. Developing and fully expanded foliage, lower surface: 146A; venation, 147B. Petiole length: About 2 cm. Petiole diameter: About 1 cm. Petiole texture, upper and lower surfaces: Smooth, glabrous. Petiole color, upper and lower surfaces: Close to 147B to 147C.

*Reproductive leaf description.*—Arrangement: Single leaves subtending of the flowering stems; sessile. Length: About 1 cm to 5 cm. Width: About 2 cm to 4 cm. Shape: Palmately lobed. Apex: Aristate. Base: Cuneate. Margin: Palmately lobed; serrate. Texture, upper and lower surfaces: Smooth, glabrous; leathery. Color: Developing and fully expanded foliage, upper surface: Between 137A and 147A; venation, 147B. Developing and fully expanded foliage, lower surface: Between 137A and 147A; venation, 147B.

Flower description:

*Flower type and habit.*—Teasel-like flower heads arranged on erect leafy flower stems. Flowers sessile. Freely flowering habit, about five to seven flowers per lateral branch.

*Natural flowering season.*—In The Netherlands, plants flower from June through mid-October. Flowers persistent.

*Time to flower.*—Early flowering habit, plants begin flowering about 16 to 18 weeks after planting.

*Flower longevity.*—Flowers of the new *Eryngium* maintain good substance for about four to six weeks on the plant.

*Flower diameter.*—About 8 mm to 15 mm.

*Flower height.*—About 1 cm to 2 cm.

*Flower shape.*—Conical.

*Bracts.*—Quantity: About 13 per flower. Length: About 1 cm. Width: About 2 mm. Shape: Roughly lanceolate. Apex: Sharply acute. Base: Acuminate. Margin: Spiny. Texture, upper and lower surfaces: Glabrous, smooth. Bract Color: When opening and fully opened, upper surface: 137C. When opening and fully opened, lower surface: 137A overlain with 93C. From a distance, overall flower color appears to be close to 94A.

*Peduncles.*—Length: About 8 cm to 14 cm. Diameter: About 2 mm. Angle: Erect. Strength: Strong. Texture: Smooth, glabrous. Color, immature: 193A. Color, mature: Between 93C and 97C.

*Reproductive organs.*—Stamens: Anther length: About 2 mm. Anther color: 94C. Filament length: About 3 mm. Filament color: 97C. Pollen color: 91D. Pollen Amount: Moderate. Pistils: Pistil length: About 3 mm to 4 mm. Style color: 94A. Stigma color: 94A.

*Seeds/fruit.*—Seed and fruit development have not been observed.

Disease/pest resistance: Resistance to known pathogens and pests common to *Eryngium* has not been observed on plants of the new *Eryngium* grown under commercial greenhouse conditions.

Temperature tolerance: Plants of the new *Eryngium* have been observed to tolerate temperatures from about −10° C. to about 30° C.

It is claimed:

1. A new and distinct cultivar of *Eryngium* plant named 'Little Blue Wonder', as illustrated and described.

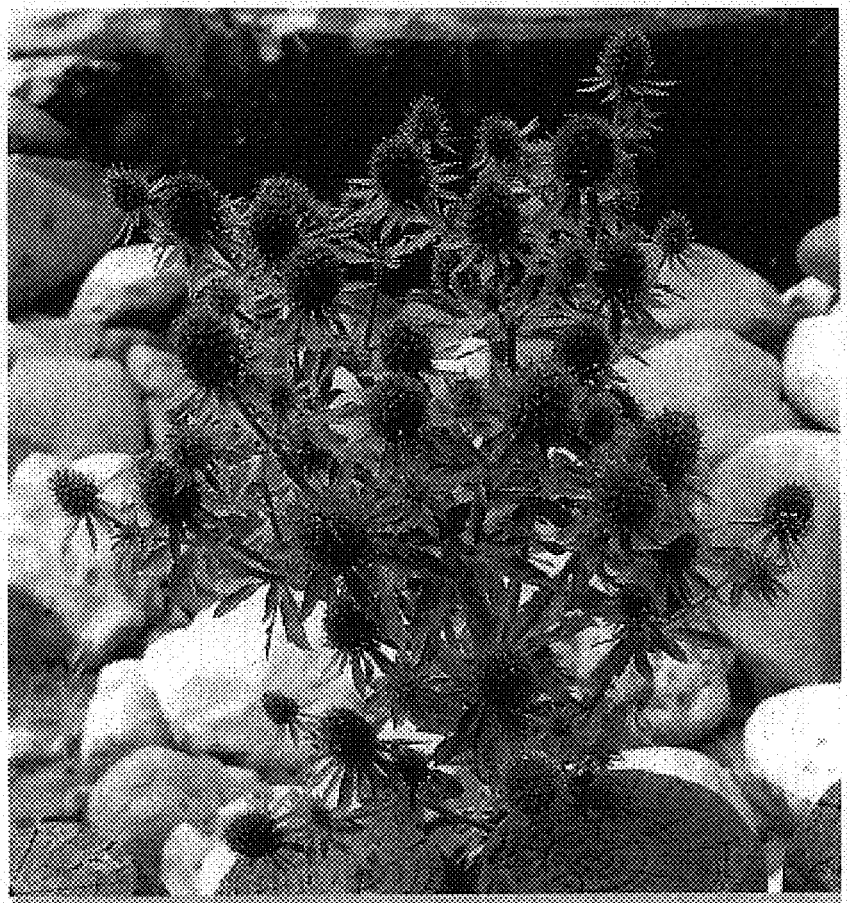
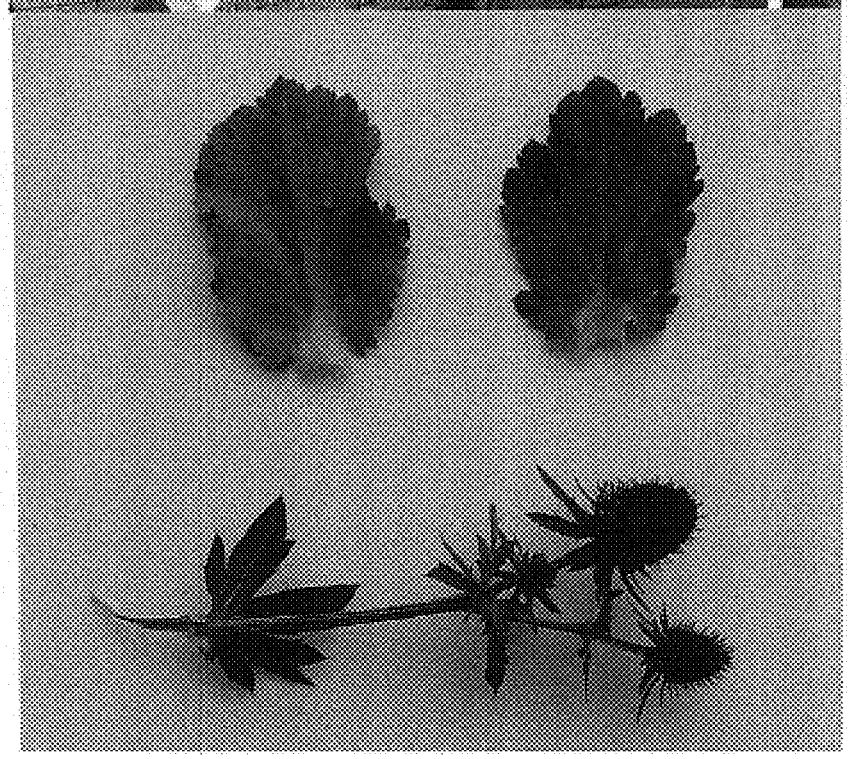

* * * * *